(12) United States Patent
Flynn

(10) Patent No.: US 8,674,119 B2
(45) Date of Patent: Mar. 18, 2014

(54) CHEMICAL PROCESSES FOR THE MANUFACTURE OF SUBSTITUTED BENZOFURANS

(75) Inventor: Bernard Luke Flynn, Donvale (AU)

(73) Assignee: Bionomics Limited, Thebarton, South Australia (AU)

( * ) Notice: Subject to any disclaimer, the term of this patent is extended or adjusted under 35 U.S.C. 154(b) by 0 days.

(21) Appl. No.: 13/810,364

(22) PCT Filed: Jul. 15, 2011

(86) PCT No.: PCT/AU2011/000900
§ 371 (c)(1),
(2), (4) Date: Mar. 7, 2013

(87) PCT Pub. No.: WO2012/006686
PCT Pub. Date: Jan. 19, 2012

(65) Prior Publication Data
US 2013/0211102 A1    Aug. 15, 2013

(30) Foreign Application Priority Data
Jul. 16, 2010    (AU) ................................ 2010903175

(51) Int. Cl.
*C07F 9/14*    (2006.01)
*C07D 307/88*    (2006.01)

(52) U.S. Cl.
USPC ........................................ 549/220; 549/468

(58) Field of Classification Search
USPC ................................ 549/220, 468
See application file for complete search history.

(56) References Cited

U.S. PATENT DOCUMENTS

2011/0130367 A1    6/2011    Kremmidiotis et al.

FOREIGN PATENT DOCUMENTS

| AU | 2009240878 A1 | 6/2011 |
| WO | WO 2007/087684 A1 | 8/2007 |
| WO | WO 2011/022772 A1 | 3/2011 |
| WO | WO 2011/022781 A1 | 3/2011 |
| WO | WO 2011/063469 A1 | 6/2011 |

OTHER PUBLICATIONS

Gill et al, J. of Organic Chemistry, vol. 73, Supporting Information, p. S1 to S4 (2008).*
Gill, G.S., et al., "An Efficient Synthesis and Substitution of 3-Aroyl-2-bromobenzo[*b*]furans," *J. Org. Chem.*, 73(3):1131-1134 (2008).
Kremmidiotis, G., et al., "BNC105: A Novel Tubulin Polymerization Inhibitor That Selectively Disrupts Tumor Vasculature and Displays Single-Agent Antitumor Efficacy," *Mol. Cancer Ther.*, 9(6):1562-1573 (2010).
International Search Report, International Application No. PCT/AU2011/000900; Dated: Sep. 26, 2011.

* cited by examiner

*Primary Examiner* — Bernard Dentz
(74) *Attorney, Agent, or Firm* — Hamilton, Brook, Smith & Reynolds, P.C.

(57) ABSTRACT

The present invention relates to the scaled-up synthesis of biologically active compounds which display useful therapeutic activity in treating proliferative disorders. In particular the invention relates to process methods for the kilogram scale synthesis of a particular class of substituted benzofuran tubulin polymerisation inhibitors.

18 Claims, No Drawings

CHEMICAL PROCESSES FOR THE MANUFACTURE OF SUBSTITUTED BENZOFURANS

This application is the U.S. National Stage of International Application No. PCT/AU2011/000900, filed Jul. 15, 2011, which designates the U.S., published in English, and claims priority under 35 U.S.C. §§119 or 365(c) to Australian Application No. 2010903175, filed Jul. 16, 2010.

FIELD OF INVENTION

The present invention relates to the scaled-up synthesis of biologically active compounds which display useful therapeutic activity in treating proliferative disorders. In particular the invention relates to process methods for the kilogram scale synthesis of a particular class of substituted benzofuran tubulin polymerisation inhibitors.

BACKGROUND OF THE INVENTION

WO 2002/060872 (PCT/AU2002/000099) and WO 2007/087684 (PCT/AU2007/000101) discloses, inter alia, substituted benzofuran compounds of the following general class:

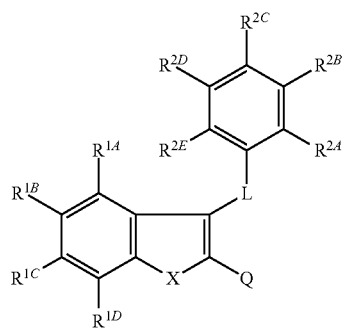

These compounds have been shown to possess promising anti-proliferative activity as tubulin polymerisation inhibitors (TPIs)

While the synthesis of the 2-aryl-3-aroyl-benzofuran class has been quite successful on a laboratory scale (that is, less than 10 gram scale) the use of this methodology to efficiently produce larger amounts (i.e., kilogram scale) of this and other preferred 2-substituted 3-aroyl-benzofurans has proven to be challenging. This has caused the present inventors to devise new scale up methodology to overcome the current deficiencies which exist in the art. The present invention is directed to addressing these shortcomings to enable an efficient kilogram scale synthesis of a preferred class of substituted benzofurans which display unique TPI activity.

SUMMARY OF INVENTION

In one aspect, the invention provides a method of preparing kilogram quantities of compounds of formula (1)

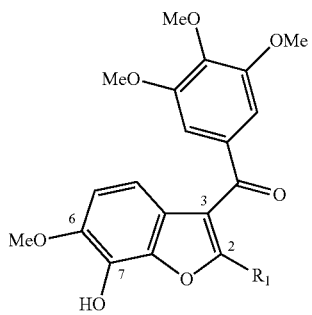

or a C-7 disodium phosphate ester thereof, wherein $R_1$ is an optionally substituted $C_1$-$C_4$ alkyl, optionally substituted $C_2$-$C_4$ alkenyl or optionally substituted $C_2$-$C_5$ alkynyl;

said method comprising the steps of a) coupling a compound of formula (2) with an alkyne of formula (3) in the presence of a palladium catalyst

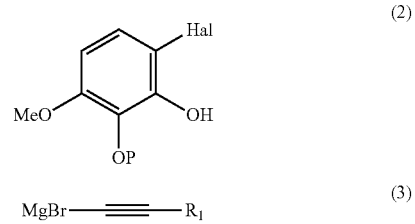

wherein Hal is I or Br, and

P is a hydroxy protecting group;

b) reacting in situ the resultant coupled product of step a) with a compound of formula (4)

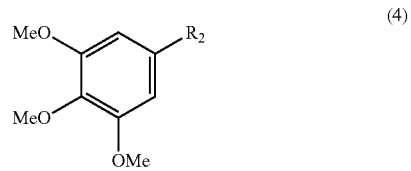

wherein $R_2$ is Br, I or $CF_3SO_3$, in the presence of CO at a temperature below 50° C.; and c) removing the C-7 hydroxy protecting group to obtain a compound of formula (1) and optionally converting the C-7 hydroxy group into the disodium phosphate ester thereof.

In an embodiment step c) involves removing the C-7 hydroxy protecting group and converting the hydroxy group into the C-7 disodium phosphate ester thereof. Accordingly in another aspect the invention provides a method of preparing kilogram scale quantities of compounds of formula (1a)

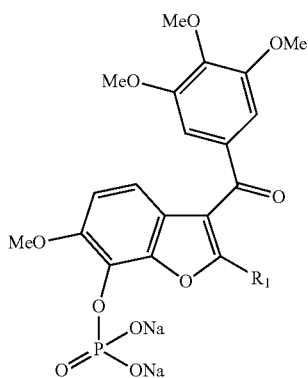

(1a)

wherein $R_1$ is as defined above.

In a further aspect the invention provides a method of preparing kilogram scale quantities of a compound of formula (1a), said method comprising the steps of:

a) coupling a compound of formula (2) with an alkyne of formula (3) in the presence of a palladium catalyst

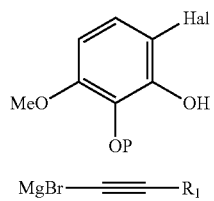

(2)

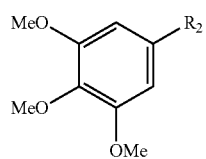

(3)

wherein Hal is I or Br,
P is a hydroxy protecting group; and
$R_1$ is an optionally substituted $C_1$-$C_4$ alkyl, optionally substituted $C_2$-$C_4$ alkenyl or optionally substituted $C_2$-$C_5$ alkynyl;

b) reacting in situ the resultant coupled product with a compound of formula (4)

(4)

MeO, R_2
MeO
OMe wherein $R_2$ is Br, I, or $CF_3SO_3$,
in the presence of CO at a temperature below 50° C.;

c) treating the resultant compound with tributylphosphine to enable the substantial removal of the palladium catalyst; and d) optionally removing the C-7 hydroxy protecting group to obtain a compound of formula (1); and, e) optionally converting the C-7 hydroxyl group into the disodium phosphate ester to obtain a compound of formula (1a).

DETAILED DESCRIPTION OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The invention is based on the discovery that compounds of the general formula (1) and (1a), as described in the above Summary of the Invention can be prepared efficiently, in good-high yields and with high purity in kilogram quantities by adopting specific reaction conditions which are described in more detail herein below.

The term "alkyl" refers to a straight or branched chain saturated hydrocarbon group, such as methyl ("Me"), ethyl ("Et"), n-propyl, isopropyl, n-butyl and the like.

Preferably, and in respect of the above formulae $R_1$ is $C_{1-3}$ alkyl and even more preferably methyl and ethyl. In a more preferred embodiment $R_1$ is methyl.

"Alkenyl" refers to a monovalent alkenyl group which may be straight chained or branched. Examples include ethenyl (—CH=CH$_2$), n-propenyl (—CH$_2$CH=CH$_2$), iso-propenyl (—C(CH$_3$)=CH$_2$), but-2-enyl (—CH$_2$CH=CHCH$_3$), and the like.

"Alkynyl" refers to a monovalent alkynyl group having one carbon to carbon triple bond. Examples of alkynyl groups include ethynyl (—C≡CH), propargyl (—CH$_2$C≡CH), pent-2-ynyl (—CH$_2$C≡CCH$_2$—CH$_3$), and the like.

The term "optionally substituted" means that a group may include one or more substituents. One or more hydrogen atoms on the group may be replaced by substituent groups independently selected from halogens, $C_{1-6}$ alkyl, $C_{2-6}$ alkenyl, $C_{2-6}$ alkynyl, —(CH$_2$)$_p$$C_{3-7}$ cycloalkyl, —(CH$_2$)$_p$$C_{4-7}$ cycloalkenyl, —(CH$_2$)$_p$ aryl, —(CH$_2$)$_p$ heterocyclyl, —(CH$_2$)$_p$ heteroaryl, —C$_6$H$_4$S(O)$_q$C$_{1-6}$ alkyl, —C(Ph)$_3$, —OCF$_3$, —CF$_3$, —CN, —OR, —O—(CH$_2$)$_{1-6}$—R, —O—(CH$_2$)$_{1-6}$—OR, —OC(O)R, —C(O)R, —C(O)OR, —OC(O)NR'R", —NR'R", —NRC(O)R', —NRC(O)NR'R", —NRC(S)NR'R", —NRS(O)$_2$R', —NRC(O)OR', —C(NR)NR'R", —C(=NOR')R, —C(=NOH)NR'R", —C(O)NR'R", —C(=NCN)—NR'R", —C(=NR)NR'R", —C(=NR')SR", —NR'C(=NCN)SR", —CONRSO$_2$R', —C(S)NR'R", —S(O)$_q$R, —SO$_2$NR'R", —SO$_2$NRC(O)R', —OS(O)$_2$R, —PO(OR)$_2$ and —NO$_2$;

where p is 0-6, q is 0-2 and each R, R' and R" is independently selected from H, $C_{1-6}$ alkyl, $C_{2-6}$ alkenyl, $C_{2-6}$ alkynyl, $C_{3-7}$ cycloalkyl, $C_{4-7}$ cycloalkenyl, aryl, heterocyclyl, heteroaryl, $C_{1-6}$ alkylaryl, $C_{1-6}$ alkylheteroaryl, and $C_{1-6}$ alkylheterocyclyl, wherein the alkyl, alkenyl, alkynyl, cycloalkyl, cycloalkenyl, aryl, heterocyclyl, heteroaryl, $C_{1-6}$ alkylaryl, $C_{1-6}$ alkylheteroaryl, or $C_{1-6}$ alkylheterocyclyl, may be optionally substituted with one to six of same or different groups selected from halogen, hydroxy, lower alkyl, lower alkoxy, —CO$_2$H, CF$_3$, CN, phenyl, NH$_2$ and —NO$_2$; or when R' and R" are attached to the same nitrogen atom, they may, together with the atom to which they are attached, form a 5 to 7 membered nitrogen containing heterocyclic ring.

The initial process step involves coupling a compound of formula (2) with an alkyne of formula (3) in the presence of a palladium catalyst.

In a preferred embodiment 2 or more molar equivalents of the alkyne are used in the coupling reaction relative to formula (2). More preferably about 2 molar equivalents of (3) are used in the coupling reaction relative to (2). The first equivalent of the Grignard metallates the phenol and the second equivalent couples to the resulting phenoxide of (2). In this embodiment, the preferred alkyne (3) is 1-propynyl magnesium bromide. Even more preferably the alkyne (3) is presented as a solution in tetrahydrofuran (THF) (for example, 0.50 M of 1-propynylmagnesium bromide in THF, available from Aldrich). An alternative approach would be to prepare the magnesium phenoxide using one equivalent of a Grignard reagent, such as methyl magnesium bromide or isopropyl magnesium bromide, then to couple the resulting phenoxide with about one molar equivalent of (3).

In an embodiment Hal in (2) is I.

The palladium catalyst may be any suitable Pd(0) or Pd(II) complex known to be suitable in, for instance, Kumuda, Negishi, Sonogashira, Suzuki or Stille coupling chemistry. Preferably the palladium catalyst is selected from $Pd(PPh_3)_2Cl_2$ (Bis(triphenylphosphine)palladium(II) chloride), $Pd(PPh_3)_4$, $PdCl_2$, $Pd(NH_3)_2Cl_2$, $Pd(NH_3)_2(NO_2)_2$, $PdCl_2(CH_3CN)_2$, and Pd (dibenzylideneacetone)$_3$.

The palladium catalyst is present in a catalytic amount, and preferably from 0.01-0.20 molar equivalents relative to alkyne (3).

In an embodiment, Hal in (2) is I, alkyne (3) is 1-propyl-magnesium bromide and the palladium catalyst is $Pd(PPh_3)_2Cl_2$.

The coupling reaction is conducted in an inert atmosphere (e.g., nitrogen or argon) and in a polar aprotic solvent (or mixture of polar aprotic solvents) such as diethyl ether, ethyl acetate, and THF. Preferably the reaction is conducted in THF.

In an embodiment the reaction vessel is purged with an inert gas and then charged with (2), the palladium catalyst and solvent (preferably THF). The mixture is preferably cooled to about 15° C.-18° C. and a THF solution of (3) is added drop-wise, at a rate which keeps the reaction temperature below 30° C.

The coupling reaction (after the addition of all components) is preferably allowed to warm to room temperature and then heated to reflux. The reaction progress can be monitored by TLC or by HPLC.

It will be appreciated that the resultant coupled product from the above reaction will be a compound of formula (3a):

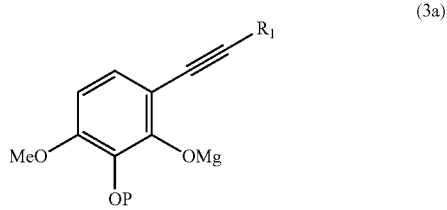

(3a)

In step (b) this product is reacted in situ with a compound of formula (4) in the presence of carbon monoxide (CO) at a temperature of below 50° C.

Preferably, prior to the addition of a compound of formula (4) and CO the solvent from step (a) is distilled, in vacuo, to around 50-75% of the original amount of solvent at which point anhydrous dimethyl sulfoxide (DMSO) is added and the distillation process is continued until most of the remaining THF (from step (a)) is removed from the reaction mixture. Accordingly, in an embodiment, the solvent for step (a) is THF and the solvent for step (b) is DMSO.

Once the solvent from step (a) is replaced with DMSO, the reaction vessel (containing (3a)) may be charged with (4) and the vessel back filled with an inert gas (e.g., nitrogen or argon). The vessel is preferably then evacuated and filled with CO (preferably between atmospheric pressure and 4 psi) and then the reaction is allowed to proceed at a temperature below 50° C.

Preferably the reaction is conducted at a temperature of between 10-40° C., and more preferably 15-30° C., and most preferably from about 25° C.-about 30° C.

On this point the present inventors have surprisingly found that when the reaction is conducted at temperatures below 50° C. (and preferably at about 30° C.) such temperatures appear to positively effect CO insertion in the heteroannulative coupling reaction. Without wanting to be bound by any particular theory it is believed that the increased CO insertion at lower temperatures may be twofold: (i) the dissolved CO gas concentration will be higher at lower temperatures, increasing CO insertion in the Pd(II) aryl intermediate to give the Pd(II) aroyl intermediate, and (ii) the Pd(II) aroyl intermediate species are more electrophilic than equivalent Pd(II) aryl intermediates and the former can undergo heteroannulative coupling to the O-alkynylphenol at a lower temperature than the Pd(II) aryl intermediates. It is further postulated that increasing the temperature increases the capacity of the less reactive Pd(II) aryl intermediate to undergo competitive heteroannulative coupling prior to CO insertion. In any event the net effect of lowering the reaction temperature greatly improves the efficiency of the reaction and aids in the reactions scalability as it minimises the need for chromatography purification of the cyclisation/carbonylation product.

As a result these conditions minimise the production of the unwanted non-CO inserted benzofuran by-product which is more prevalent in analogous reactions performed at higher temperatures. The advantages of minimising such side-products is that further purification on a large scale (i.e., for instance, the need for a chromatographic step) can be avoided.

The reaction progress may be monitored by TLC or HPLC.

In an embodiment $R_2$ is I and the reaction temperature is 25° C.-35° C., and more preferably at about 30° C.

The cyclisation/carbonylation product from this reaction is represented as formula (Ia'):

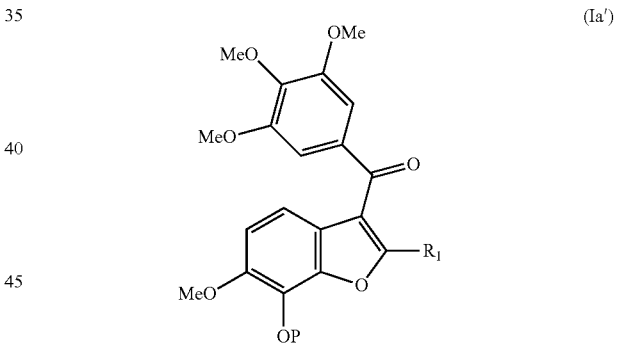

(Ia')

This product may be extracted from the reaction mixture by quenching with aqueous HCl and filtering the resultant solution. Prior to this though it is preferable that tributylphosphine is added to the crude reaction mixture to enable the removal of the Pd catalyst. Preferably the amount of tributylphosphine added is between 0.8-1.2 molar equivalents to the palladium catalyst.

In a further preferred embodiment after the completion of the above reaction steps the crude reaction mixture is again treated with about 2-4 molar equivalents of tributylphosphine relative to the palladium catalyst. The present inventors have discovered that the addition of tributylphosphine at this stage (preferably in 2 separate portions) greatly minimises the amount of Pd which may be associated with the final product (compounds of formula (1) or the salts/esters thereof). The advantage of this step is paramount to the acceptable purity of the end product. In the absence of this step unacceptable levels of Pd (i.e., levels above those accepted for heavy metals by regulatory bodies) may persist in the final product. Regulatory authorities such as the US-FDA require Pd levels in pharmaceuticals to be ideally below <10 ppm. In this embodiment the complexed tributylphosphine/Pd catalyst usually forms a precipitate which can be removed by filtration (preferably with two filtration steps firstly with a Celite pad and secondly through the use of a 0.45 μm PTFE filter). After tributylphosphine treatment, the Pd level (for instance, in the formula (I) or (Ia) compounds where $R_1$ is Me) is less than 2 ppm, which is within the acceptable levels.

Once the cyclisation/carbonylation step has been completed the C-7 hydroxyl protecting group (P) of compounds of formula (1a') may be removed. In an embodiment P is preferably an iso-propyl group. Accordingly, for instance, this group may be removed by treating the product of step (b) with boron trichloride ($BCl_3$) in dichloromethane (DCM) at low temperatures (e.g., 0° C.-10° C.).

Other suitable protecting groups for hydroxyl groups would be known to those in the art and may be found in, for instance, *Protective Groups in Organic Synthesis*, T. W. Greene and P. Wutz, John Wiley & Son, $3^{rd}$ Edition. Conditions for the removal of such groups may also be found in the above text which is incorporated herein in its entirety. Other notable protecting groups for the C-7 hydroxy group may include branched alkyl ethers such as —O-sec-butyl, —O-tert-butyl, along with —Otrityl, —OPMB, and the like.

The unprotected C-7 hydroxyl group may then be converted to a phosphate ester or a salt of said ester. In a preferred embodiment the C-7 hydroxy group is converted to the disodium phosphate ester thereof to obtain a compound of formula (1a).

In this reaction the compound of formula (1) is initially treated with a non-nucleophilic base such as triethylamine (TEA), and then subsequently with phosphoryl chloride at lower temperatures (e.g., −10° C.-0° C.). This reaction may be conducted in a chlorinated solvent such as dichloromethane.

The disodium salt of the phosphate intermediate produced may be achieved by adding an aqueous NaOH solution to a solution of the intermediate, preferably in acetonitrile.

As a further preferred embodiment the salt produced (compound of formula (1a)) can be removed from the reaction mixture by filtration (under partial vacuum), and preferably washed with ether and dried at atmospheric pressure. Preferably, the drying step is conducted at room temperature and at atmospheric pressure and has been found to be important in order to maintain maximal stability of the phosphate ester and for achieving acceptably low levels of compounds of formula (1) in the final disodium phosphate ester product (1a). In this regard, it has been found that levels of (1) below 2% will ensure dissolution into a pharmaceutically acceptable vehicle such as a 0.9% saline solution.

Accordingly, from the above, it will also be appreciated that a further important intermediate in the manufacture of compounds of formula (I) and (Ia') is the substituted halophenols of formula (2):

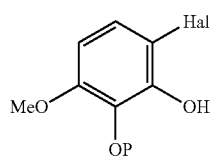

(2)

wherein P is a suitable protecting group as described above.

As such in a further aspect the invention provides a method of preparing kilogram quantities of compounds of formula (2) including the steps of:

(a) protecting the 2-hydroxy group of o-vanillin to form (2a);

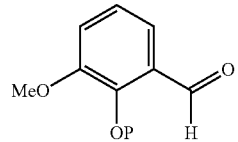

(2a)

(b) oxidizing (2a) and saponifying the intermediate formate ester to form (2b); and

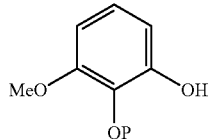

(2b)

(c) halogenating (2b) to form (2).

Therefore the invention also contemplates the use of the reaction steps (a)-(c) in the manufacture of formula (2) which in turn may be subjected to the additional process steps described herein to prepare kilogram scale amounts of compounds of formula (I) or (Ia').

In an embodiment and with specific reference to process steps (a) to (c) above, P is an iso-propyl group. Accordingly, in an embodiment, step (a) involves the treatment of o-vanillin with 2-bromopropane. Preferably this reaction is performed in the presence of a weak base such as potassium carbonate. Alternative bases may include caesium carbonate, sodium carbonate or sodium hydride. The Baeyer-Villiger oxidation for the aldehyde to a formate ester may be performed using m-chloroperbenzoic acid (m-CPBA) in dichloromethane (DCM). An alternative method is to use hydrogen peroxide as the oxidising agent. The formate ester may be saponified using aqueous sodium hydroxide. Other inorganic bases, such as potassium carbonate, potassium hydroxide or lithium hydroxide, may be alternative reagents for the saponification. The reagent for iodination may be selected to provide regiospecificity for iodination ortho to the hydroxyl of the phenol. This approach has fewer steps relative to an alternative protection strategy where a protecting group directs the lithiation ortho to the oxygen. Reagents for direct iodination ortho to hydroxyl groups include iodine/copper(II) acetate, iodine/silver trifluoroacetate, and iodine/tertbutylamine.

The following examples are intended to illustrate the invention and are not to be construed as being limitations thereon.

EXAMPLES

Example 1

Step a)+b)

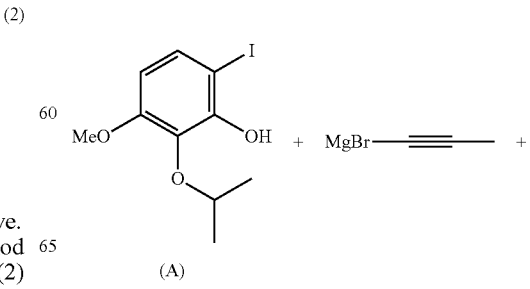

(A)

-continued

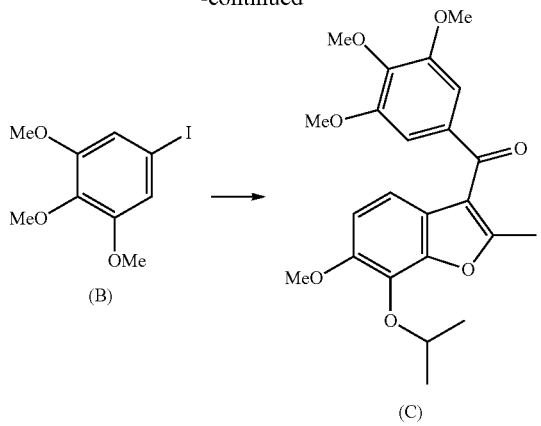

All reagents were sourced from Sigma-Aldrich
1. A dry 12 L three neck round bottom flask was purged with N₂. Compound (A) (200 g, 649.1 mmol), bis(triphenylphosphine)palladium(II) chloride (23 g, 32 mmol) and anhydrous THF (1.3 L) were added to the flask under N₂. The flask was then flushed with N₂ for 5 min. The mixture was then cooled with a water bath (15-18° C.) and a 0.5 M 1-propynylmagnesium bromide solution (1.4 mol in anhydrous THF 2.8 L) was added whilst maintaining the internal temperature <30° C. Caution: propyne gas is generated during addition.
2. After addition, the solution was heated to reflux for 5-9 h under a N₂ atmosphere. The reaction was monitored by TLC (30% EtOAc/hexane; UV and PMA) or HPLC.
3. The reaction mixture was concentrated, in vacuo, at 35° C. (water bath temperature) to remove about ¾ of the solvent. Anhydrous DMSO (2.4 L) was then added and removal of THF continued until complete (a point when the distillate comes out at a significantly slower rate).
4. The 12 L flask was then equipped with an overhead stirrer (through an air-tight adapter), gas inlet tap with balloon attached and a thermocouple. Compound (B) (229 g, 779 mmol) was then added and the flask evacuated and back-filled twice with N₂. The balloon was then filled with CO and the flask evacuated and filled twice with CO and the mixture vigorously stirred and heated to 30±5° C. for 12-18 h. The reaction was monitored by TLC (30% EtOAc/hexane; PMA) or HPLC (Spec: intermediate is <3% or the intermediate decreases in a rate of <2% per hour).
5. Once the reaction had reached completion, tributylphosphine (32 mL, 130 mmol) was added and the reaction mixture was stirred for a further 30 min.
6. Ice cold water (2.4 L) was then added, at once giving a slurry, 1 M HCl solution (380 mmol in water 380 mL) was added and the mixture stirred for 10 min. to achieve a pH 4-5 (the slurry turned into nice filterable slurry below pH 5). The precipitate was filtered through a class C frit funnel, washed with water (800 mL), methanol (600 mL) and again with methanol (400 mL).
7. The collected solid was dissolved in DCM (400 mL); further DCM can be used if needed to achieve full dissolution. To the solution was added tributylphosphine (20 mL, 80 mmol) and the mixture stirred for 0.5 h. The solution was filtered through a Celite pad (pre washed with DCM), rinsing with further DCM (100 mL). The filtrate was then filtered through a 0.45 micron PTFE filter and the solution was concentrated, in vacuo at 30-40° C. (water bath temperature) until a thick slurry resulted (end volume ~350 mL). With stirring, to the slurry, was added methanol (600 mL) in two portions, after the first portion (~300 mL) was added, the resulting slurry was concentrated again, in vacuo, to ~400 mL; after the second portion was added, the slurry was again concentrated, in vacuo, to ~300-400 mL. The mixture was at this stage filtered through class C frit funnel. The collected solid was washed with methanol (200 mL) and dried under high vacuum at 40-50° C. over 5 h, giving the product as a white solid. Yield: 148.72 g (55.3%). R_f=0.43 (30% EtOAc/hexane). HPLC shows 100% purity.

Step c)

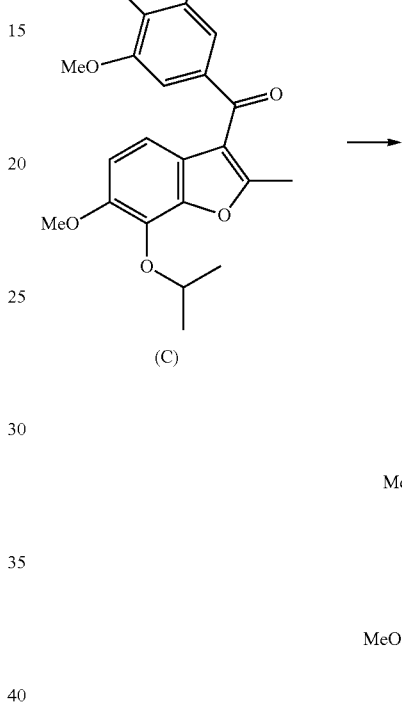

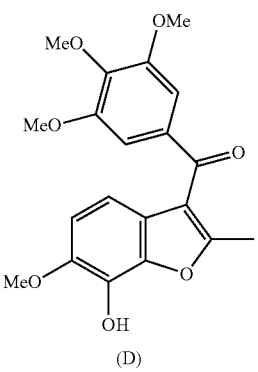

1. A 3 L three neck round bottom flask was equipped with an overhead stirrer, addition funnel and thermocouple/N₂ inlet. To the flask was added (C) (147.5 g, 355.9 mmol) and anhydrous DCM (740 mL) under a N₂ atmosphere and the solution cooled with an ice water bath. When internal temperature was <5° C., a 1 M BCl₃ solution (360 mmol in DCM 360 mL) was added via the addition funnel whilst maintaining the internal temperature <20° C. (addition time ~1 min; T max=15.1° C.)
2. Once the exothermic reaction had finished the ice water bath was removed and the mixture was allowed to stir at RT for 1-1.5 h, monitoring the reaction by TLC (50% EtOAc/hexane; spot the reaction mixture directly on TLC plate) showed the reaction to be ~40% complete at this stage. After the addition of two further lots of the 1 M BCl₃ solution (72 mmol in DCM 72 mL) in the manner outlined above with 1-1.5 h of reaction time at RT between lots, TLC showed the reaction to be complete. HPLC showed 0.55% starting material remaining.
3. The reaction mixture was cooled to 5° C. and a 10% aqueous NH₄Cl solution (830 mmol in water 440 mL) was carefully added and the mixture stirred for 10 min (a small amount of precipitate was observed). To this mixture was added methanol (300 mL) and most of the solids dissolved. The bottom, DCM layer, was separated and the aqueous layer was extracted with a mixture of DCM (150 mL) and methanol (44 mL).

Note: Additional amount of the DCM/methanol solvent mixture and water can be used to help the extraction should an emulsion form.

4. The combined DCM/methanol extracts were concentration, in vacuo, to ~⅔ of the volume (~450 mL). Methanol (300 mL) was added and concentrated, in vacuo, again to ~⅔ of the volume (300-450 mL). The mixture was filtered, and washed with methanol (150 mL).
5. The collected solid was dried under high vacuum at 40-50° C. to give pale yellow solid. Yield: 122.6 g (92.5%). HPLC showed purity of 99.06%. (Pd content: 1.7 ppm, measured by Inductively Coupled Plasma Mass Spectrometry (ICPMS)).

Step d)

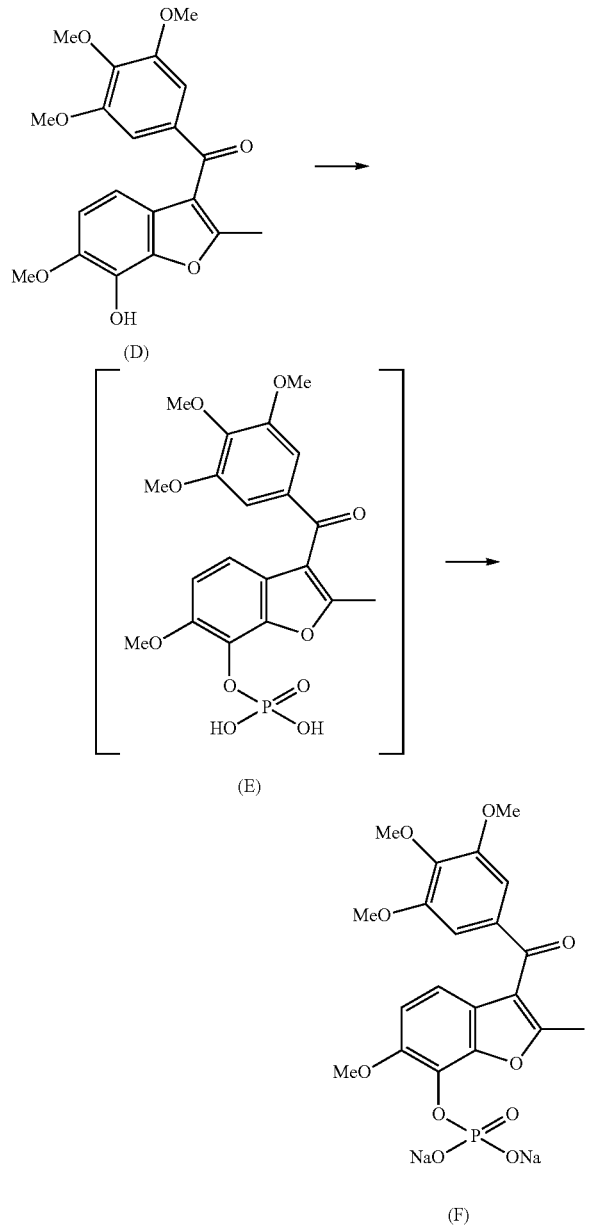

1. A 2 L three neck round bottom flask was equipped with addition funnel, thermocouple and an overhead stirrer and the flask purged with N$_2$. To the flask was added (D) (112.3 g, 301.6 mmol) and anhydrous DCM (550 mL) and stirred to give an orange slurry. Triethylamine (61.8 mL, 443 mmol) was added via the addition funnel and stirred for 30 min. to give a hazy orange solution.

Note: Slight exotherm: T=12-15° C.

2. Another 2 L three neck round bottom flask was equipped with addition funnel, thermocouple and overhead stirrer. The flask was purged with nitrogen and to the flask was added anhydrous DCM (550 mL) and phosphoryl chloride (68.8 mL, 738 mmol). The solution was then cooled with an ice-methanol bath and when the internal temperature reached –10° C., with rapid stirring, the prepared (D)/DCM/triethylamine mixture was added dropwise via the addition funnel whilst maintaining the internal temperature <3° C. (addition time ~20 min.). The flask and addition funnel were rinsed with DCM (20 mL) into to the reaction mixture. After addition, the mixture was stirred at between –10 and 0° C. for 10 min. The mixture was then concentrated, in vacuo, at 30° C. (water bath temperature) to give an orange slurry.
3. To the resulting slurry was added toluene (235 mL) and the slurry was concentrated, in vacuo, at 40° C. (water bath temperature) to give an orange solid. To the solid was added acetonitrile (220 mL) and the solvent was removed again, in vacuo, at 40° C. (water bath temperature).
4. To the flask containing the product was attached a thermocouple, overhead stirrer and additional funnel and to this was added acetonitrile (330 mL). With rapid stirring, the slurry was cooled with an ice water bath. When the internal temperature reached <–5° C., a 1 M solution of NaOH (1.3 mol, in water 1.3 L) was slowly added maintaining the internal temperature <35° C. (Note: only the addition of the first few mLs are very exothermic; pH ~13-14). The solution was concentrated, in vacuo, at 40° C. (water bath temperature) to give an orange solid.
5. To the flask containing the solid was attached an additional funnel, thermocouple and overhead stirrer and water (200 mL) was added and the mixture stirred (pH~3-4). A 1 M solution of NaOH (484 mmol in water 484 mL) was added until the pH stabilized at ~10-11 (addition time ~0.5 h).
6. A Celite plug was prepared (~7-8 cm tall in a 600 mL sized class C frit funnel), the Celite was slurried in water and drained; washed with acetone and ample water until the water filtrate is nearly clear (Note: water must be the last wash). The product mixture (at pH ~10-11) was filtered through the Celite pad and rinsed with water (100 mL). At this stage the filtrate is a greenish yellow and weighted 1171 g, pH ~11. The filtrate was transferred into a 5 L three neck round bottom flask.
7. The flask was attached with overhead stirrer, addition funnel and thermocouple and cooled with a water bath. With good stirring, concentrated HCl (37:63, HCl:water, 70 mL) was added via the addition funnel until a pH ~0-2 was reached and a thick off-white slurry was obtained. To this was added DCM (1 L) followed by methanol (1 L) and a clear biphasic solution resulted. The pH of the aqueous layer was checked to make sure the pH was ~0-2. The organic layer was separated and the aqueous layer was extracted with DCM (100 mL).
8. The combined organic layers were dried over anhydrous Na$_2$SO$_4$ (100 g) with stirring for ~20 min. The solution was filtered and concentrated, in vacuo, at 30° C. (water bath temperature) and further dried at RT until weight change <2% over 0.5 h to give the crude acid (120 g).
9. To the flask containing the product was attached an overhead stirrer, thermocouple and addition funnel. The flask was cooled with a water bath and methanol (200 mL) was added. To this was added a 1 M solution of NaOH (500 mmol, in water 500 ml) portion-wise over 25 min., until the pH stabilized at ~10-11.

10. The slurry was concentrated, in vacuo, at 40° C. (water bath temperature) and weighted 390 g (target weight is three to four times (360-480 g) that of the crude acid (120 g)). The slurry was an almost clear dark solution with pH ~9-10 containing only a few small orange solid chunks. The flask was equipped with an overhead stirrer and a 1 M solution of NaOH (5 mmol, in water 5.0 mL) was added with stirring (10 min.) to adjust pH to ~10-11 at which point the orange solids were nearly all dissolved.

11. With rapid stirring, acetonitrile (2.06 L) was added to the slurry and the mixture stirred for 30-60 min. The resulting mixture was then filtered through a class C frit funnel washing the solid with acetonitrile (220 mL), diethyl ether (220 mL) and again with diethyl ether (220 mL). Once filtrate stopped dripping, vacuum was maintained for a further 10-20 min. and a creamy solid was obtained. The solid was transferred onto a glass drying pan; covered with a layer of Kimwipe and dried in an isolator with air passing over the surface.

12. The material was packed in amber bottles after a total of 42 h in air in an isolator. Yield: 134 g (89.5%). HPLC (three runs, by average): 99.18%. ICP showed 8.5% Na and 5.1% P. KF shows 11.1% water. Residual solvent test showed diethyl ether 2997 ppm and acetonitrile 100 ppm. DCM, methanol and toluene were not detected.

Example 2

1) Preparation of Substituted Iodophenol Starting Material (III)

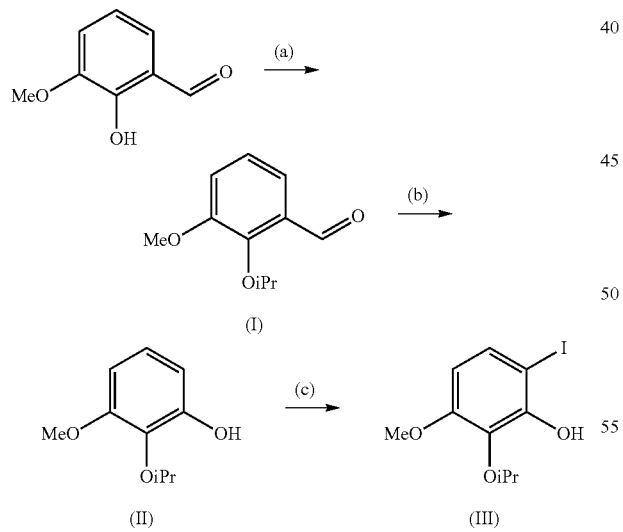

(a): Formation of Isopropyl Ether (I)

The reaction vessel was charged with anhydrous DMF (35 L) under nitrogen, then o-vanillin (7.0 kg, 46 mol) and $K_2CO_3$ (15 kg, 109 mol) were added at RT. 2-Bromopropane (7.0 L, 75 mol) was slowly added slowly at RT. The reaction mixture was set to reflux at 110° C. until determined by TLC and HPLC to be complete (1.5 h). The reaction mixture was allowed to cool to RT and water (50 L) was added to the mixture. The reaction mixture was extracted with EtOAc (3×50 L). The pooled organics were washed with water (8×25 L) and saturated aqueous NaCl solution (25 L) and dried over $Na_2SO_4$ (5 kg). The organics were concentrated to give pure liquid compound (I). Yield: 8.9 kg (quant.)

(b): Baeyer-Villiger Oxidation of the Aldehyde (II)

The reaction vessel was charged with (2) (8.9 kg, 46 mol) followed by anhydrous DCM (180 L) and cooled to 0-5° C. m-CPBA (75%, 20 kg, 87 mol) was then added portion-wise whilst maintaining temperature of the reaction mixture in the range 0-5° C. The mixture was stirred at RT for 18 h and determined to be complete by TLC. The precipitate was filtered and washed with anhydrous DCM (20 L), the filtrate was distilled to give a residue, which was then dissolved in methanol (180 L). A solution of NaOH (3.8 kg, 95 mol) in water (5.3 L) was added and the mixture was stirred for 2 h at RT. The methanol was distilled and the residue was diluted with saturated aqueous $NH_4Cl$ solution (35 L) and extracted with EtOAc (3×50 L). The pooled organics were washed with water (2×40 L), saturated aqueous NaCl solution (40 L) and dried over $Na_2SO_4$ (5 kg). The organics were concentrated to give pure liquid compound (II). Yield: 8.4 kg (quant.).

(c): Iodination Ortho to the Phenol (III)

The reaction vessel was charged with a solution of iodine (17 kg, 67 mol) in acetic acid (90 L) and (II) (8.4 kg, 46 mol) was added. $Cu(CO_2CH_3)_2.H_2O$ (10 kg, 50 mol) was added and the reaction mixture was heated at 55° C. for 22 h and determined to be complete by TLC. The acetic acid was distilled and EtOAc (100 L) was added to the residue. The organic layer was washed with aqueous $Na_2S_2O_3$ solution (5×25 L), water (3×50 L), saturated aqueous NaCl solution (50 L) and dried over $Na_2SO_4$ (5 kg). The volatiles were distilled off and the crude product was purified by column chromatography using 60-120 Silica and 10% EtOAc in petroleum ether as eluent. Yield: 2.5 kg (18%)

2) Multicomponent Coupling to Afford (V)

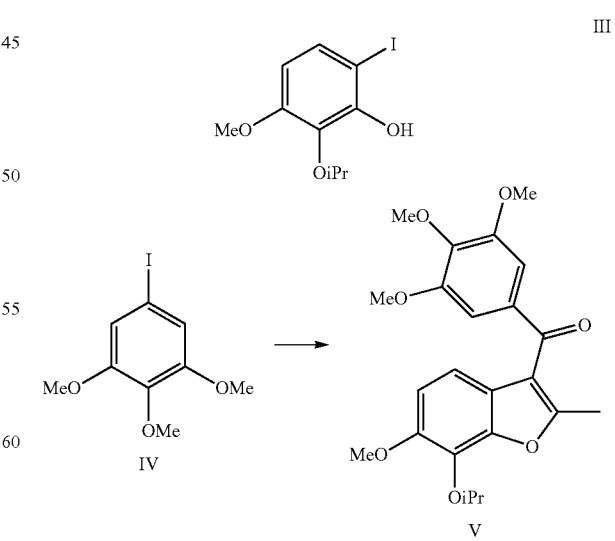

1. A 50 gallon glass-lined reactor was purged with $N_2$ and the jacket temperature was set to 22.5° C. (III) (2.286 kg, 7.419 mol) and bis(triphenylphosphine)palladium(II) chloride (0.253 kg, 0.360 mol) and anhydrous THF (14.3 kg) were added. The reactor was then flushed with N₂ for 5 min. The mixture was then cooled to 16° C. and a 0.5 M 1-propynylmagnesium bromide solution in THF (16.0 mol, 30.3 kg) was added over 19 minutes maintaining the internal temperature <30° C. Caution: propyne gas is generated during addition.

2. After addition, the solution was heated to reflux for 9 h. The reaction was monitored by HPLC and judged to be complete when the amount of (III) was less than 3%.

3. The reaction mixture was concentrated by solvent exchange distillation at <35° C. to remove ~½ solvent. Anhydrous DMSO (29.9 kg) was added and the remaining THF was removed under vacuum at <35° C.

4. The reactor was refilled with N₂ and equipped with a gas inlet. 1-iodo-3,4,5-trimethoxybenzene (IV) (2.585 kg, 8.790 mol) was added. The mixture was evacuated and back-filled with nitrogen, then evacuated and back-filled with CO twice. The gas regulator was adjusted to add 1-4 psi of CO to the reactor. The reaction mixture was stirred at 195 rpm and heated to 30° C. for 39 h and monitored by HPLC.

5. After the reaction was shown to be complete, CO was vented and the reactor was purged with N₂ for 8 minutes. The reaction temperature was maintained at 30° C. and tributylphosphine (0.297 kg, 0.936 mol) was added and the reaction mixture was stirred for 30 min.

6. RO/DI water (27.3 L) at 1° C. was added at once giving a slurry. An aqueous HCl solution (37% HCl, (0.54 kg) and water (4.5 L)) was made up in a 10 L Nalgene bottle and 4.35 kg of this solution was added to the slurry in the reaction vessel and stirred for 17 min to give a final pH ~5. The precipitates were filtered through a Nutsche filter, pressing with N₂ and then washed with water (10 L), again pressing with N₂. Methanol (6.0 kg) was added to the residue and the material was slurried for 15 minutes and then pressed with N₂. The procedure was repeated with methanol (3.70 kg). The solid was dried under N₂ in the Nutsche filter at 22.5° C. for 59 hours.

7. The solid was transferred to an appropriate sized three neck round bottom flask with overhead stirring and a gas inlet and dissolved in DCM (4.6 L). To the solution was added tributylphosphine (234 mL, 937 mmol) and the mixture stirred for 39 min. The solution was filtered through a 10 cm Celite pad that was pre-washed with DCM and the round bottom flask rinsed with DCM (1.18 L), which was used to rinse the Celite pad. The filtrate was then filtered through a 0.45 micron PTFE Omnipore hydrophilic membrane filter, rinsing with DCM (450 mL) and then again with DCM (225 mL). The filtrate was concentrated on a rotorvap at <40° C. until a thick slurry resulted (solvent was not removed to dryness). With stirring, to the slurry was added methanol (6.8 L) in two portions. After the first portion (~½ volume) was added, the resulting slurry was concentrated again but not to dryness; after second portion was added, the slurry was concentrated again to a final mass of 5.29 kg. The slurry was then filtered through class C sintered glass funnel and the collected solid was washed with methanol (2.2 L). The product was left on the filter under vacuum and argon bleed for 16 h, then transferred to an isolator vacuum oven and dried under high vacuum at ambient temperature for 16 h giving the product (V) as a white solid. Yield: 1475 g (48%). HPLC shows 99.82% purity.

3) Deprotection of Isopropyl Ether (V) to Afford (VI)

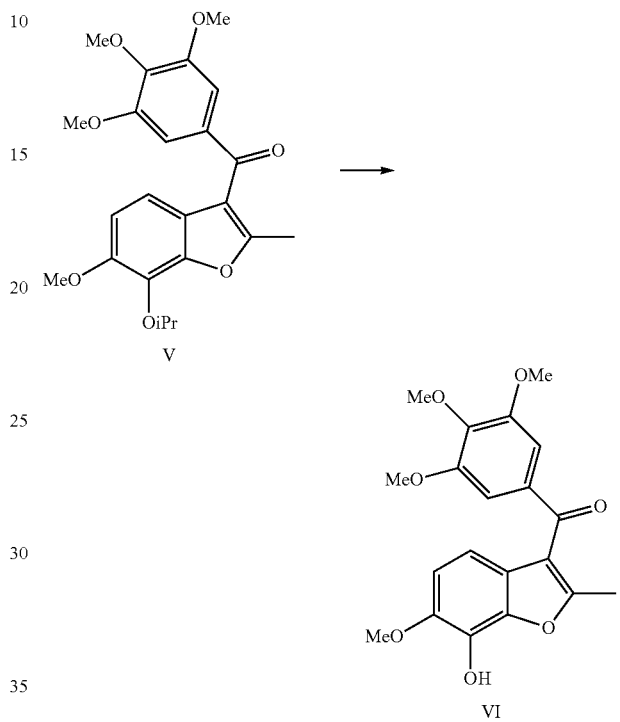

1. An appropriately sized three neck round bottom flask was equipped with an overhead stirrer, addition funnel, thermocouple and an argon inlet. To the flask, was added, (V) (1475 g, 3.56 mol) and anhydrous DCM (7.4 L) and the solution cooled <5° C. with an ice water bath. When the internal temperature was 2.2° C., a 1.0 M solution of BCl₃ in DCM (3698 mL, 3.70 mol) was added in two portions (~½ volume) to maintain the internal temperature <20° C. (addition time for portion 1 1858 mL=14 min; T max=8.0° C., addition time for portion 2, 1840 mL=104 min; T max=8.2° C.).

2. The cooling bath was removed and the mixture was allowed to warm to RT and stirred for 81 min. TLC (50% EtOAc/hexane; spot the reaction mixture directly on TLC plate; R_f=0.36) of the mixture showed the reaction to be incomplete. To the mixture at 20° C. a 1.0 M of solution of BCl₃ in DCM (700 mL, 0.7 mol) was added over 3 min. (T max=22.9° C.) and stirred for 1.5 h, after which time the reaction was incomplete. Another portion of the 1.0 M solution of BCl₃ in DCM (710 mL, 0.71 mol) was added over 21 min. (T max=21.6° C.) and stirred for 3.5 h, after which time the reaction was incomplete. Another portion of the 1.0 M solution of BCl₃ in DCM (352 mL, 0.352 mol) was added over 7 min. (T max=20.4° C.) and stirred for 1.5 h, after which time TLC showed the reaction to be complete.

3. The reaction mixture was cooled to 3.8° C. and an aqueous NH₄Cl solution (451.05 g, in RO/DI water 4.0 L) was carefully added over 37 min. (Caution: very exothermic and off-gassing at beginning, T max=19.9° C.) and stirred for 11 min. To the quenched mixture methanol (3.0 L) was added and the layers were mixed thoroughly for 11 min. The layers were allowed to separate and the bottom DCM layer was collected. The aqueous layer was extracted further with a mixed solvent of DCM (1480 mL) and methanol (440 mL) and the layers were mixed thoroughly for 6 min and allowed to separate and the DCM layer collected and combined with the previously collected DCM layer.

4. The combined extracts were concentrated on a rotorvap to approximately three times the weight of the starting material (2605 g). Methanol (3.0 L) was added and the mixture concentrated on a rotorvap again this time to 3686 g. The mixture was then filtered on a Class C sintered funnel and the collected solids washed with methanol (1.45 L). The solids were dried under vacuum at RT for 3 days to give compound VI as a pale yellow solid. Yield: 1209 g (91%). HPLC purity: 96.13%.

Note: In Example 1 the palladium content was measured at this time using ICP-MS and Pd: 1.7 ppm.

4) Phosphate Ester Formation to Afford (VII)

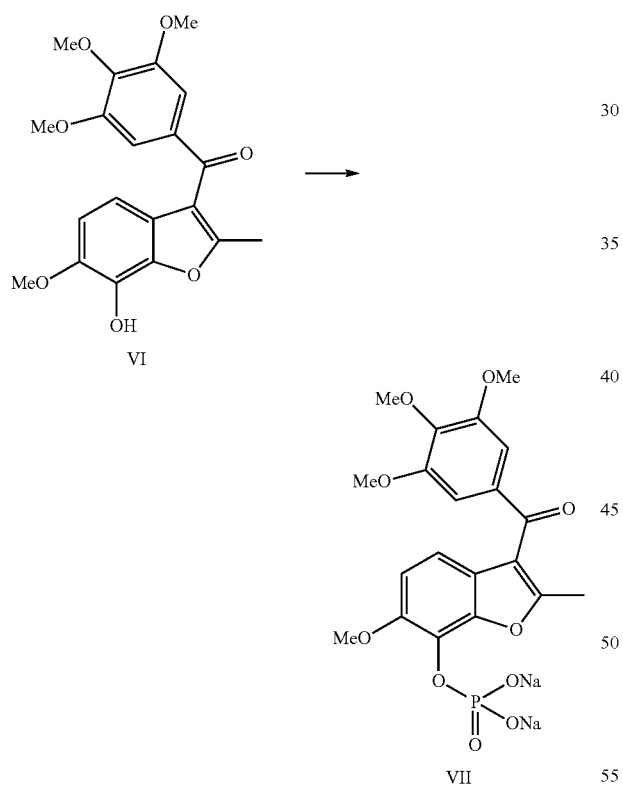

1. An appropriately sized three neck round bottom flask was equipped with a thermocouple and an overhead stirrer. The flask was purged with argon and (VI) (1209 g, 3.247 mol) and anhydrous DCM (6.0 L) were added and stirred to give an orange slurry. Triethylamine (670 mL, 4.807 mol) was slowly added and stirred for 50 min. to give a hazy orange solution.

2. Another, three necked round bottom flask, was equipped with an addition funnel, thermocouple, overhead stirrer and gas inlet. The flask was purged with argon and to this flask was added anhydrous DCM (6.0 L) and phosphoryl chloride (740 mL, 7.94 mol). This solution was cooled with ice-methanol bath for 32 min. and when the internal temperature reached −7.6° C., with rapid stirring, the prepared (VI)/DCM/triethylamine mixture was added drop-wise over 51 min. via addition funnel to maintain the internal temperature below −1.7° C. The flask and addition funnel was rinsed with DCM (265 mL) and the rinse was added to the reaction mixture. After addition, the mixture was stirred at between −15 and −5° C. for 15 min. The mixture was then concentrated on a rotorvap to dryness at <40° C. to give an orange slurry.

3. To the resulting slurry was added toluene (2.45 L) and the slurry was concentrated, in vacuo, (<40° C.) to dryness to give an orange solid. To the solid was added acetonitrile (2.55 L) and the solvent was removed again, in vacuo, (<40° C.).

4. The flask containing the product was attached with thermocouple, overhead stirrer, addition funnel and gas outlet and acetonitrile (3975 mL) was added. With rapid stirring, the slurry was cooled with an ice water bath and when the internal temperature reached 4.7° C. (48 min.), a 1.0 M solution of NaOH in RO/DI water (14.1 L, cooled to 4° C.) was slowly added over 30 min. (T max=18.0° C.), to reach pH 13 (Note: only the addition of the first few mLs are very exothermic). The solution was concentrated to dryness, in vacuo, (<40° C.) to give an orange solid.

5. The flask containing the solid was equipped with a thermometer, gas outlet and overhead stirrer and with rapid stirring, RO/DI water (2.5 L) was added (pH ~8). A 1.0 M solution of NaOH in RO/DI water (4.5 L) was added portion-wise (~1 L at a time) over ~5 hours until the pH stabilized at ~11.

6. A Celite plug was prepared (10 cm tall in class C frit funnel). The Celite was slurried in water and drained; washed with acetone and ample water until the water filtrate is nearly clear (Note: water must be the last wash). The hazy product mixture was filtered through the Celite pad; rinsed with RO/DI water (1.2 L) and the filtrate (pH ~12) transferred into a three neck round bottom flask.

7. The flask was attached with overhead stirrer, addition funnel, gas outlet and thermocouple and cooled with tap water bath. With rapid stirring, a 37% HCl solution (730 mL) was added, over 12 min. until pH 0 was attained and a thick off-white slurry was obtained. To the slurry was added DCM (10.875 L), followed by methanol (10.87 L) and the layers were mixed thoroughly for 7 min. until a clear biphasic solution resulted (pH of the aqueous layer was 0). The organic layer was separated and the aqueous layer further extracted with DCM (1.2 L).

8. The combined organic layers were dried over anhydrous $Na_2SO_4$ (1226 g) with stirring for 21 min. The solution was filtered through a Class C glass funnel, washing with sufficient DCM and the filtrates were concentrated to dryness, in vacuo, (<40° C.) and further dried at RT, in vacuo, until weight change <2% over 0.5 h to give the crude acid (2108 g)

9. The flask containing the product was attached with overhead stirrer, thermocouple and gas outlet and cooled with a tap water bath. Methanol (2.4 L) was added followed by portion-wise (~1 L at a time) addition of a 1.0 M NaOH solution (4645 mL) in RO/DI water with rapid stirring over ~3 h, until the pH stabilized at ~10-11 (T max=24.9° C.).

10. The slurry was concentrated on the rotorvap (<40° C.) to a weight of 4483 g with pH 8. The flask was equipped with overhead stirrer and a 1.0 M NaOH solution (355 mL) in RO/DI water was added portion-wise (~100 mL at a time) to adjust pH to 11 with 10-15 min. stirring between additions (T max=27.3° C.).

11. With rapid stirring acetonitrile (22.5 L) was added and the resulting mixture was stirred for 60 min. and filtered through a class C fit funnel using only partial vacuum and without a blanket of inert gas. The collected solid was washed with acetonitrile (3.62 L) and diethyl ether (3.6 L) and once the filtrate stopped dripping, vacuum was maintained for a further 16 min. and a creamy solid was obtained. The solid was loosed and transferred onto a glass drying pan; covered with a layer of Kimwipe and dried in an isolator at RT and atmospheric pressure with air passing through the surface for 47 h until weight change <0.5% over 1 h.

12. The material (VII) was packed in amber bottles. Yield: 1393 g, (86%). HPLC: 99.94%. ICP-MS showed 7.4% Na, 6.2% P and Pd none detected. KF shows 12.8% water. Residual solvent test showed diethyl ether 713 ppm; acetonitrile, DCM, methanol and toluene not detected.

The invention claimed is:

1. A method of preparing kilogram quantities of a compound of formula (1)

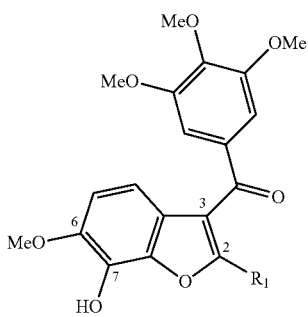

(1)

or a C-7 disodium phosphate ester thereof, wherein $R_1$ is an optionally substituted $C_1$-$C_4$ alkyl, optionally substituted $C_2$-$C_4$ alkenyl or optionally substituted $C_2$-$C_5$ alkynyl;

said method comprising the steps of:

a) coupling a compound of formula (2) with an alkyne of formula (3) in the presence of a palladium catalyst

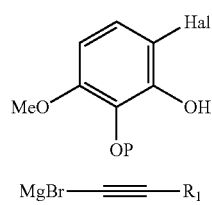

(2)

(3)

wherein Hal is I or Br, and

P is a hydroxy protecting group;

b) reacting in situ the resultant coupled product of step a) with a compound of formula (4)

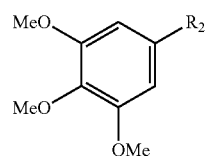

(4)

wherein $R_2$ is Br, I or $CF_3SO_3$, in the presence of CO at a temperature below 50° C.; and c) removing the C-7 hydroxy protecting group to obtain a compound of formula (1) and optionally converting the C-7 hydroxy group into the disodium phosphate ester thereof.

2. A method of preparing kilogram scale quantities of a compound of formula (1a),

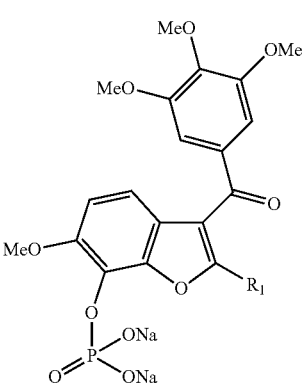

(1a)

said method comprising the steps of:

a) coupling a compound of formula (2) with an alkyne of formula (3) in the presence of a palladium catalyst

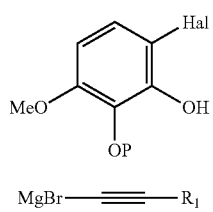

(2)

(3)

wherein Hal is I or Br,

P is a hydroxy protecting group; and $R_1$ is an optionally substituted $C_1$-$C_4$ alkyl, optionally substituted $C_2$-$C_4$ alkenyl or optionally substituted $C_2$-$C_5$ alkynyl;

b) reacting in situ the resultant coupled product with a compound of formula (4)

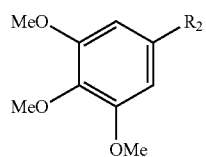
(4)

wherein $R_2$ is Br, I, or $CF_3SO_3$,
in the presence of CO at a temperature below 50° C.;
c) treating the resultant compound with tributylphosphine to enable the substantial removal of the palladium catalyst; and
d) removing the C-7 hydroxy protecting group to obtain a compound of formula (1); and,

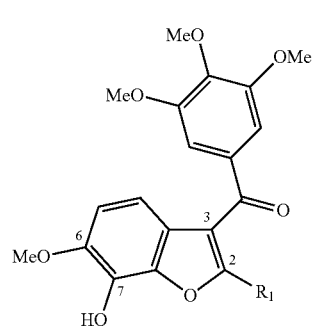
(1)

e) converting the C-7 hydroxyl group into the disodium phosphate ester to obtain a compound of formula (1a).

3. A method according to claim 1 wherein the palladium catalyst is bis(triphenylphosphine)palladium(II)chloride.

4. A method according to claim 1 wherein the compound of formula (3) is 1-propynylmagnesium bromide.

5. A method according to claim 1 wherein P of compounds of formula (2) is iso-propyl.

6. A method according to claim 1 wherein $R_2$ of compounds of formula (4) is iodo.

7. A method according to claim 1 wherein the temperature of the CO insertion step is between about 25-35° C.

8. A method according to claim 7 wherein the CO insertion step is conducted at 1-4 psi of CO.

9. A method of preparing kilogram quantities of a compound of formula (1)

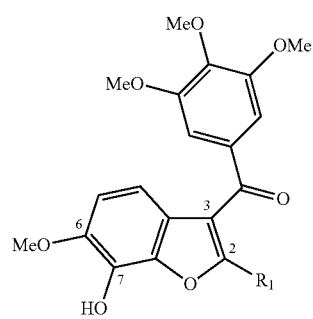
(1)

or a C-7 disodium phosphate ester thereof,
wherein $R_1$ is an optionally substituted $C_1$-$C_4$ alkyl, optionally substituted $C_2$-$C_4$ alkenyl or optionally substituted $C_2$-$C_5$ alkynyl;

said method comprising the steps of:
(a) protecting the 2-hydroxy group of o-vanillin to form a compound of formula (2a);

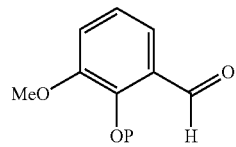
(2a)

(b) oxidizing (2a) with m-CPBA followed by saponification with an inorganic base to form a compound of formula (2b);

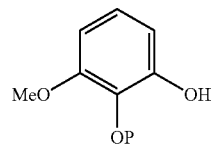
(2b)

(c) halogenating (2b) to form a compound of formula (2);
(d) coupling a compound of formula (2) with an alkyne of formula (3) in the presence of a palladium catalyst

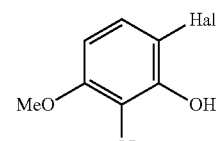
(2)

(3)

wherein Hal is I or Br, and
is a hydroxy protecting group;
(e) reacting in situ the resultant coupled product of step (d) with a compound of formula (4)

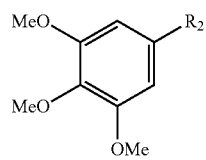
(4)

wherein $R_2$ is Br, I or $CF_3SO_3$,
in the presence of CO at a temperature below 50° C.; and
(f) removing the C-7 hydroxy protecting group to obtain a compound of formula (1) and optionally converting the C-7 hydroxy group into the disodium phosphate ester thereof.

10. A method of preparing kilogram scale quantities of a compound of formula (1a),

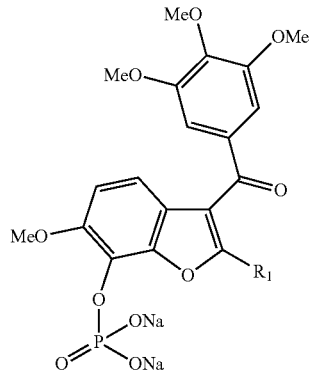
(1a)

said method comprising the steps of:

(a) protecting the 2-hydroxy group of o-vanillin to form a compound of formula (2a);

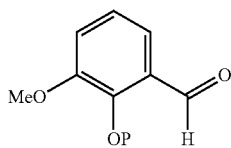
(2a)

(b) oxidizing (2a) with m-CPBA followed by saponification with an inorganic base to form a compound of formula (2b);

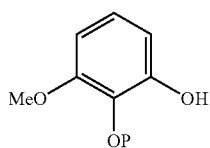
(2b)

(c) halogenating (2b) to form a compound of formula (2);

(d) coupling a compound of formula (2) with an alkyne of formula (3) in the presence of a palladium catalyst

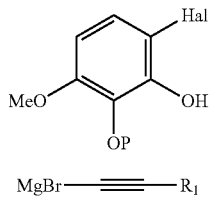
(2)

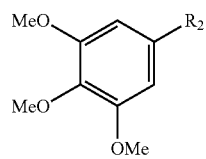
(3)

wherein Hal is I or Br,
P is a hydroxy protecting group; and
$R_1$ is an optionally substituted $C_1$-$C_4$ alkyl, optionally substituted $C_2$-$C_4$ alkenyl or optionally substituted $C_2$-$C_5$ alkynyl;

(e) reacting in situ the resultant coupled product with a compound of formula (4)

$$\text{(4)}$$

wherein $R_2$ is Br, I, or $CF_3SO_3$,
in the presence of CO at a temperature below 50° C.;

(f) treating the resultant compound with tributylphosphine to enable the substantial removal of the palladium catalyst; and (g) removing the C-7 hydroxy protecting group to obtain a compound of formula (1); and, (h) converting the C-7 hydroxyl group into the disodium phosphate ester to obtain a compound of formula (1a).

11. A method according to claim 9 wherein the palladium catalyst is bis(triphenylphosphine)palladium(II)chloride.

12. A method according to claim 9 wherein the compound of formula (3) is 1-propynylmagnesium bromide.

13. A method according to claim 9 wherein P of compounds of formula (2) is iso-propyl.

14. A method according to claim 9 wherein $R_2$ of compounds of formula (4) is iodo.

15. A method according to claim 9 wherein the temperature of the CO insertion step is between about 25-35° C.

16. A method according to claim 15 wherein the CO insertion step is conducted at 1-4 psi of CO.

17. A method according to claim 1, where $R_1$ is $C_1$-$C_4$ alkyl.

18. A method according to claim 17, wherein $R_1$ is methyl.

* * * * *